US010105433B2

United States Patent
Chandran et al.

(10) Patent No.: US 10,105,433 B2
(45) Date of Patent: Oct. 23, 2018

(54) METHODS AND ASSAYS FOR TREATING HANTAVIRUS INFECTIONS

(71) Applicant: ALBERT EINSTEIN COLLEGE OF MEDICINE, INC., Bronx, NY (US)

(72) Inventors: Kartik Chandran, Brooklyn, NY (US); Thijin R. Brummelkamp, Amsterdam (NL); Lucas T. Jae, Amsterdam (NL); Rohit K. Jangra, Bronx, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 15/118,504

(22) PCT Filed: Feb. 25, 2015

(86) PCT No.: PCT/US2015/017410
§ 371 (c)(1),
(2) Date: Aug. 12, 2016

(87) PCT Pub. No.: WO2015/130722
PCT Pub. Date: Sep. 3, 2015

(65) Prior Publication Data
US 2017/0173141 A1    Jun. 22, 2017

Related U.S. Application Data

(60) Provisional application No. 61/944,287, filed on Feb. 25, 2014.

(51) Int. Cl.
| | | |
|---|---|---|
| *C07K 16/28* | (2006.01) | |
| *A61K 39/12* | (2006.01) | |
| *A61K 31/7105* | (2006.01) | |
| *A61K 31/7084* | (2006.01) | |
| *G01N 33/53* | (2006.01) | |
| *G01N 33/15* | (2006.01) | |

(52) U.S. Cl.
CPC .......... *A61K 39/12* (2013.01); *A61K 31/7084* (2013.01); *A61K 31/7105* (2013.01); *G01N 33/15* (2013.01); *G01N 33/53* (2013.01); *A61K 2121/00* (2013.01); *G01N 2500/00* (2013.01)

(58) Field of Classification Search
None
See application file for complete search history.

(56) References Cited

U.S. PATENT DOCUMENTS

| 9,234,885 B2 | 1/2016 | Chandran et al. |
| 9,346,875 B2 | 5/2016 | Lai et al. |
| 2014/0018338 A1 | 1/2014 | Chandran et al. |

FOREIGN PATENT DOCUMENTS

| WO | 2010043650 A2 | 4/2010 |
| WO | 2012083475 A1 | 6/2012 |
| WO | 2012105931 A2 | 8/2012 |

OTHER PUBLICATIONS

Connie Schmaljohn, Vaccine, 2009, 27:D61-D64. (Year: 2009).*
Jung et al., The Journal of Infectious Diseases, 2018, XX00:1-4. (Year: 2018).*
PCT International Search Report and Written Opinion, dated Jun. 11, 2015 in connection with PCT International Application No. PCT/US2015/17410,11 pages.
Li Y H et al., entitled "Fast Preparation of a Polyclonal Antibody Against Chicken Protocadherin 1," Genet Mol Res., Jun. 28, 2013, vol. 12, No. 2, pp. 2156-2166.
Van Hateren N J et al., entitled FatJ acts via the Hippo Mediator Yap1 to Restrict the Size of Neural Progenitor Cell Pools, Development, May 15, 2011, vol. 138, No. 10, pp. 1893-1902.
Jin M et al., entitled "Hantaan Virus Enters Cells by Clathrin-Dependent Receptor-Mediated Endocytosis," Virology, Mar. 1, 2002, vol. 294, No. 1, pp. 60-69.
Li Y et al., entitled "Elevated Vascular Endothelial Growth Factor Levels Induce Hyperpermeability of Endothelial Cells in Hantavirus Infection," J Int Med Res., Oct. 2012, vol. 40, No. 5; pp. 1812-1821.

* cited by examiner

*Primary Examiner* — Stacy B Chen
(74) *Attorney, Agent, or Firm* — Amster, Rothstein & Ebenstein LLP

(57) ABSTRACT

Methods and assays are disclosed for treating a subject with a hantavirus infection using an agent that binds to protocadherin-1 (PCDH1) or inhibits expression of protocadherin-1 (PCDH1).

8 Claims, 7 Drawing Sheets

Specification includes a Sequence Listing.

A

```
         U2OS-WT: ACGCCCCCAAGTTTGAGCGGCCCTCCTATGAGGCCGAACTATC
PCDH1-#1 allele 1: ACGCCCCCAAGTTTGAGCGGCCCTCCT i1 ATGAGGCCGAAC
PCDH1-#1 allele 2: ACGCCCCCAAGTTTGAGCGGCCCTCCT i1 ATGAGGCCGAAC
```

METHODS AND ASSAYS FOR TREATING HANTAVIRUS INFECTIONS

CROSS-REFERENCE TO RELATED APPLICATIONS

This application is a U.S. national stage entry under 35 U.S.C. § 371 of PCT International Patent Application No. PCT/US2015/017410, filed Feb. 25, 2015, which claims the benefit of U.S. Provisional Patent Application No. 61/944,287, filed Feb. 25, 2014, the contents of which are incorporated herein by reference into the subject application.

STATEMENT OF GOVERNMENT SUPPORT

This invention was made with government support under grant number AI101436 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Hantaviruses are members of the family Bunyaviridae of enveloped viruses with segmented negative-sense RNA genomes. While hantaviruses maintain persistent infections in their rodent, shrew, or bat hosts without apparent disease symptoms, the spillover of these viruses into humans can lead to one of two serious illnesses—hantavirus pulmonary syndome (HPS) (in the New World) and hemorrhagic fever with renal syndrome (HFRS) (in Asia and Europe). Nephropathia epidemica (NE) is a milder form of HFRS endemic to Scandinavia and northern Europe. Intrusion of humans and their domestic animals into sylvatic environments, and other anthropogenic disturbances to natural systems, such as climate change, likely account for the increased frequency of zoonotic hantavirus outbreaks. Mortality from HPS and HFRS have reached 60% and 12%, respectively, in some outbreaks. Treatment is currently limited to supportive care—there are no approved vaccines or therapeutics to treat HPS/HFRS. Sin Nombre virus (SNV) and Andes virus (ANDV) are responsible for the majority of morbidity and mortality in the New World due to HPS. Hantaan virus (HTNV), Seoul virus (SEOV), Puumula virus (PUUV), and Dobrava virus (DOBV) account for most of the HFRS cases in the Old World.

The present invention addresses the need for methods and assays for treating subjects infected with hantaviruses or who are at risk for infection with hantaviruses.

SUMMARY OF THE INVENTION

The present invention provides methods for treating a subject infected with a hantavirus or for preventing an infection with a hantavirus in a subject at risk for infection with a hantavirus, where the methods comprise administering to the subject an agent that binds to protocadherin-1 (PCDH1) or inhibits expression of protocadherin-1 (PCDH1) in an amount effective to treat and/or prevent infection with a hantavirus.

The present invention also provides methods for screening for an agent that treats and/or prevents infection of a subject with a hantavirus, where the methods comprise determining whether or not the agent binds to protocadherin-1 (PCDH1) or inhibits expression of protocadherin-1 (PCDH1), wherein an agent that binds to protocadherin-1 (PCDH1) or inhibits expression of protocadherin-1 (PCDH1) is a candidate for treating and/or preventing an infection with a hantavirus.

BRIEF DESCRIPTION OF THE DRAWINGS

FIG. 2A-2B. A. (Top) Two independent U2OS cell clones with frameshift mutations in PCDH1 were generated by genome engineering. Both clones are predicted to express a truncated ~285-amino acid polypeptide. U2OS-WT-SEQ ID NO:1, PCDH1-#1 allele 1 -SEQ ID NO:2, PCDH1-#1 allele 2 -SEQ ID NO:2. (Bottom) WT and mutant U2OS clones, and mutant cells ectopically expressing human PCDH1 (+cDNA) were challenged with rVSVs bearing Andes (ANDV), Hantaan (HTNV), and VSV glycoproteins. Infection was monitored by fluorescent microscopy of cells to detect virus-encoded eGFP. B. Quantitation of infected cells from panel A. Infection was normalized to that observed in WT U2OS cells for each virus (100%).

FIG. 3A-3C. A. The first extracellular cadherin domain of PCDH1 (EC1) is required for cell entry and infection by ANDV and SNV. Wild-type human PCDH1, or mutant PCDH1 proteins lacking the first (ΔEC1) or second (ΔEC2) extracellular cadherin domains or the cytoplasmic domain (ΔCTD), were ectopically expressed in a mutant U2OS cell line lacking PCDH1. These cell lines were challenged with rVSVs bearing Andes virus (ANDV), Sin Nombre virus (SNV), Hantaan virus (HTNV), or VSV glycoproteins. Infection was monitored by fluorescent microscopy of cells to detect virus-encoded eGFP (bright cells). B. (Left) Quantitation of infected cells from panel A. (Right) Quantitation of infection of these cell lines by the authentic hantaviruses under BSL-4 containment. Infection was normalized to that observed in WT U2OS cells for each virus (100%). C. Cells expressing each PCDH1 construct were immunostained to reveal similar levels of PCDH1 expression and cell-surface localization. Cell nuclei are stained with a DNA stain, Hoechst 33342.

FIG. 5. sPCDH1-EC1/EC2 blocks cell entry and infection mediated by ANDV but not HTNV. Authentic hantaviruses, ANDV or HTNV, were pre-incubated with purified sPCDH1-EC1/EC2 for 1 h at 37° C., and the reaction mixtures were transferred to U2OS cells. Infection was monitored by immunostaining of the cells to detect viral antigen, and normalized to that obtained in the absence of sPCDH1-EC1/EC2 protein for each virus (100%).

DETAILED DESCRIPTION OF THE INVENTION

Figures 1A, 1B:
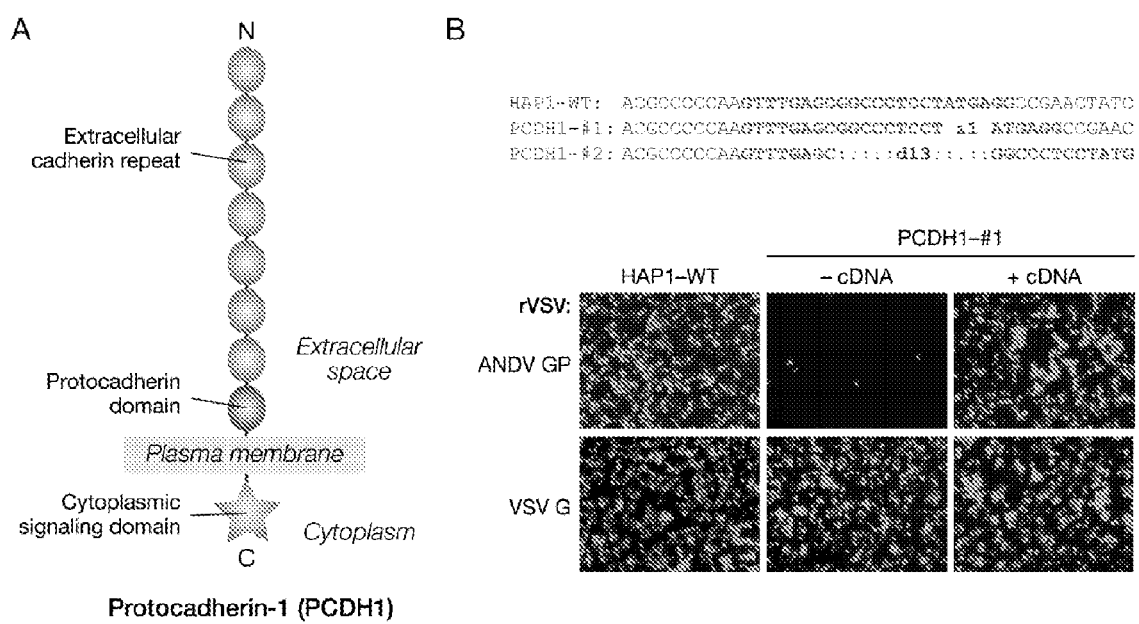
FIG. 1A-1B. Domain structure of protocadherin-1 (PCDH1). Arrow indicates approximate position at which PCDH1 is C-terminally truncated in the HAP1-PCDH1 mutant clones described in panel B. B. (Top) Two independent HAP1 cell clones with frameshift mutations in PCDH1 were generated by genome engineering. Both clones are predicted to express a truncated ~285-amino acid polypeptide. HAP1-WT-SEQ ID NO:1, PCDH1-#1 -SEQ ID NO:2, PCDH1-#2 -SEQ ID NO:3. (Bottom) WT and mutant HAP1 clones, and mutant cells ectopically expressing human PCDH1 (+cDNA) were challenged with rVSVs bearing hantavirus and VSV glycoproteins. Infection was monitored by fluorescent microscopy of cells to detect virus-encoded eGFP.

The present invention provides a method for treating a subject infected with a hantavirus or for preventing an infection with a hantavirus in a subject at risk for infection with a hantavirus comprising administering to the subject an agent that binds to protocadherin-1 (PCDH1) or inhibits expression of protocadherin-1 (PCDH1) in an amount effective to treat and/or prevent infection with a hantavirus.

Hantaviruses are members of the family Bunyaviridae of enveloped viruses. Hantavirus infection can occur due to, for example, one or more of Sin Nombre virus (SNV), Andes virus (ANDV), Hantaan virus (HTNV), Seoul virus (SEOV), Puumula virus (PUUV) and Dobrava virus (DOBV). New World hantaviruses include, e.g., Andes Virus, Sin Nombre Virus, New York Virus and Black Creek Canal Virus . Old World hantaviruses include, e.g., Hantaan Virus, Seoul Virus, Puumala Virus and Dobrava-Belgrade virus. Agents that bind to protocadherin-1 (PCDH1) or inhibit expression of protocadherin-1(PCDH1) are preferentially effective against infection by New World hantaviruses.

Hantavirus infection can result in, for example, one or more of hantavirus pulmonary syndome (HPS), hemorrhagic fever with renal syndrome (HFRS), and nephropathia epidemica (NE).

To treat a subject with a hantavirus infection means to reduce or stop the spread of hantavirus in the subject, or to eliminate the hantavirus from the subject, or to reduce or eliminate a sign or symptom of hantavirus infection in the subject. Preferably, the agent prevents entry of hantavirus into cells of a subject.

Subjects who are at risk for infection with hantavirus include subjects who have been exposed to hantavirus or are at risk of exposure to hantavirus. In addition to the natural occurrence of hantaviruses, there is the potential for exposure to these pathogens if they are used as agents of bioterrorism or biological warfare. Subjects at risk for exposure to hantavirus include first responders, medical and military personnel, biosafety level ¾ personnel and animal workers.

The agent can be, for example, an antibody, antibody fragment, aptamer or small molecule that specifically binds to protocadherin-1 (PCDH1) and reduces its activity or interferes with its normal function. Antibody fragments include, but are not limited to, F(ab')$_2$ and Fab' fragments and single chain antibodies. F(ab')$_2$ is an antigen binding fragment of an antibody molecule with deleted crystallizable fragment (Fc) region and preserved binding region. Fab' is ½ of the F(ab')$_2$ molecule possessing only ½ of the binding region. The term antibody is further meant to encompass polyclonal antibodies and monoclonal antibodies. The antibody can be a human antibody or a non-human antibody such as a goat antibody or a mouse antibody. Antibodies can be "humanized" using standard recombinant DNA techniques. Aptamers are single stranded oligonucleotides or oligonucleotide analogs that bind to a particular target molecule, such as a protein. Thus, aptamers are the oligonucleotide analogy to antibodies. However, aptamers are smaller than antibodies. Their binding is highly dependent on the secondary structure formed by the aptamer oligonucleotide. Both RNA and single stranded DNA (or analog) aptamers can be used. Aptamers that bind to virtually any particular target can be selected using an iterative process called SELEX, which stands for Systematic Evolution of Ligands by EXponential enrichment.

The agent can also be a small chemical molecule that binds to protocadherin-1(PCDH1). Preferably, the small moelecule has a molecular weight of 2,000 daltons or less, more preferably 1,500 daltons or less, or 1,000 daltons or less, or 500 daltons or less.

The agent can also be an antisense molecule, a ribozyme, or a RNA interference (RNAi) molecule, such as a small interfering RNA (siRNA) molecule, that specifically inhibits expression of protocadherin-1 (PCDH1) protein. The agent can be comprised of nucleic acid (e.g., DNA or RNA) or nucleic acid mimetics (e.g., phosphorothionate mimetics) such as those known in the art.

Preferably, the agent binds to the first extra-cellular domain (EC1) of PCDH1 or prevents expression of the first extra-cellular domain (EC1) of PCDH1, or the agent binds to both the first and second extra-cellular domain of PCDH1 or prevents expression of both the first and second extra-cellular domain of PCDH1.

It is envisioned that administration of the agent to the subject would normally be limited to periods when the subject either has a hantavirus infection or when the subject has been exposed to hantavirus or is at risk of exposure to hantavirus.

The agent can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, intravenous administration, transdermal administration, intranasal administration, and administration through an osmotic mini-pump. The compounds can be applied to the skin, for example, in compositions formulated as skin creams, or as sustained release formulations or patches.

The present invention also provides a method for screening for an agent that treats and/or prevents infection of a subject with a hantavirus, the method comprising determining whether or not the agent binds to protocadherin-1 (PCDH1) or inhibits expression of protocadherin-1 (PCDH1), wherein an agent that binds to protocadherin-1 (PCDH1) or inhibits expression of protocadherin-1 (PCDH1) is a candidate for treating and/or preventing an infection with a hantavirus. The assay can be carried out, e.g., using a cell line that expresses PCDH1, and determining whether the agent binds to PCDH1 or inhibits expression of PCDH1. The method can be carried out, for example, using a enzyme-linked-immunosorbent assay (ELISA). The method can be carried out, for example, using a electro-chemiluminescence (ECL) assay. Preferably, the agent binds to the first extra-cellular domain (EC1) of PCDH1 or prevents expression of the first extra-cellular domain (EC1) of PCDH1, or the agent binds to both the first and second extra-cellular domain of PCDH1 or prevents expression of both the first and second extra-cellular domain of PCDH1.

The invention also provides an agent for treating and/or preventing infection of a subject with a hantavirus identified by any of the methods disclosed herein for screening for an agent that treats and/or prevents infection of a subject with a hantavirus. The invention further provides a pharmaceutical composition for treating and/or preventing infection of a subject with a hantavirus comprising a pharmaceutically acceptable carrier and an agent identified by any of the methods disclosed herein for screening for an agent that treats and/or prevents infection of a subject with a hantavirus.

```
Human protocadherin-1 (PCDH1) has the amino acid
sequence
                                          (SEQ ID NO: 4)
MDSGAGGRRC PEAALLILGP PRMEHLRHSP GPGGQRLLLP

SMLLALLLLL APSPGHATRV VYKVPEEQPP NTLIGSLAAD

YGFPDVGHLY KLEVGAPYLR VDGKTGDIFT TETSIDREGL

RECQNQLPGD PCILEFEVSI TDLVQNGSPR LLEGQIEVQD

INDNTPNFAS PVITLAIPEN TNIGSLFPIP LASDRDAGPN

GVASYELQAG PEAQELFGLQ VAEDQEEKQP QLIVMGNLDR

ERWDSYDLTI KVQDGGSPPR ASSALLRVTV LDTNDNAPKF

ERPSYEAELS ENSPIGHSVI QVKANDSDQG ANAEIEYTFH

QAPEVVRRLL RLDRNTGLIT VQGPVDREDL STLRFSVLAK

DRGTNPKSAR AQVVVTVKDM NDNAPTIEIR GIGLVTHQDG

MANISEDVAE ETAVALVQVS DRDEGENAAV TCVVAGDVPF

QLRQASETGS DSKKKYFLQT TTPLDYEKVK DYTIEIVAVD

SGNPPLSSTN SLKVQVVDVN DNAPVFTQSV TEVAFPENNK

PGEVIAEITA SDADSGSNAE LVYSLEPEPA AKGLFTISPE

TGEIQVKTSL DREQRESYEL KVVAADRGSP SLQGTATVLV

NVLDCNDNDP KFMLSGYNFS VMENMPALSP VGMVTVIDGD

KGENAQVQLS VEQDNGDFVI QNGTGTILSS LSFDREQQST

YTFQLKAVDG GVPPRSAYVG VTINVLDEND NAPYITAPSN

TSHKLLTPQT RLGETVSQVA AEDFDSGVNA ELIYSIAGGN

PYGLFQIGSH SGAITLEKEI ERRHHGLHRL VVKVSDRGKP

PRYGTALVHL YVNETLANRT LLETLLGHSL DTPLDIDIAG

DPEYERSKQR GNILFGVVAG VVAVALLIAL AVLVRYCRQR

EAKSGYQAGK KETKDLYAPK PSGKASKGNK SKGKKSKSPK

PVKPVEDEDE AGLQKSLKFN LMSDAPGDSP RIHLPLNYPP

GSPDLGRHYR SNSPLPSIQL QPQSPSASKK HQVVQDLPPA

NTFVGTGDTT STGSEQYSDY SYRTNPPKYP SKQVGQPFQL

STPQPLPHPY HGAIWTEVWE.
```

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Genetic Screen in Haploid Human Cells Identified Host Genes Critical for Andes Hantavirus Entry into Host Cells.

To identify host genes critical for entry by the Andes virus (ANDV), a prototypic HPS-causing New World hantavirus, a genetic screen was performed in the HAP1 line, an adherent cell line derived from the KBM7 tumor cell-derived line (Carette et al., 2011). This cell line has a haploid karyotype, allowing the generation of null mutants for most nonessential genes. A library of mutant cells was generated by retroviral gene-trap mutagenesis. This library was challenged with a recombinant vesicular stomatitis virus expressing the ANDV entry glycoprotein (rVSV-ANDV GP) to select cells refractory to infection. Candidate host genes critical for ANDV GP-dependent infection were identified from this cell population by deep sequencing. The strongest confirmed hits in this screen fell into three major classes or pathways: cholesterol biosynthesis (7 genes), the EMC complex (5 genes), and transcription factors that modulate cholesterol biosynthesis (3 genes). In addition, a singleton gene of interest was obtained, namely PCDH1, which encodes the cell-surface adhesion protein protocadherin-1.

PCDH1 is Required for Virus Entry into Cells.

To test whether PCDH1 is required for Andes virus GP-dependent infection, CRISPR/Cas9-mediated genome engineering was used to introduce indels into the single copy of PCDH1 present in HAP1 cells. Two clones (#1, #2) were isolated with mutant PCDH1 alleles encoding a truncated ~285-amino acid polypeptide lacking 5 of 7 cadherin repeats, protocadherin domain, transmembrane domain, and cytoplasmic signaling domain (FIG. 1A-B). WT and mutant HAP1 clones were challenged with rVSVs expressing glycoproteins from ANDV and VSV. ANDV GP-dependent infection was greatly diminished in the mutant cells relative to WT; however, VSV G-dependent infection was not affected. Importantly, infection was restored in mutant cells engineered to ectopically express WT human PCDH1. Therefore, the infection defect in the PCDHV-mutant cells is attributable to the loss of the PCDH1 protein. These findings demonstrate that PCDH1 is specifically required for viral entry by a pathogenic, HPS-causing New World hantavirus, ANDV.

To extend the analysis of PCDH1's role beyond a single haploid cell line, CRISPR/Cas9-mediated genome engineering was used to introduce indels into both copies of PCDH1 in the diploid U2OS human osteosarcoma cell line, a workhorse line in various areas of biomedical research. Two clones (#1, #2) were isolated with mutant PCDH1 alleles encoding a truncated ~285-amino acid polypeptide lacking 5 of 7 cadherin repeats, protocadherin domain, transmembrane domain, and cytoplasmic signaling domain (FIG. 2A). WT and mutant U2OS clones were challenged with rVSVs expressing glycoproteins from ANDV and VSV, as well as the prototypic HFRS-causing Old World hantavirus, Hantaan virus (HTNV). As seen in HAP1 cells, ANDV GP-dependent infection in U2OS cells required PCDH1, whereas VSV G-dependent infection did not. Unexpectedly, HTNV GP—dependent infection was not affected by depletion of PCDH1. These findings afford two conclusions. First, the ANDV requirement for PCDH1 is generalizable to multiple human cell lines. Second, PCDH1 is dispensable for viral entry by a pathogenic, HFRS-causing Old World hantavirus, HTNV, and may thus represent a virus clade-specific host factor.

Figure 3A:
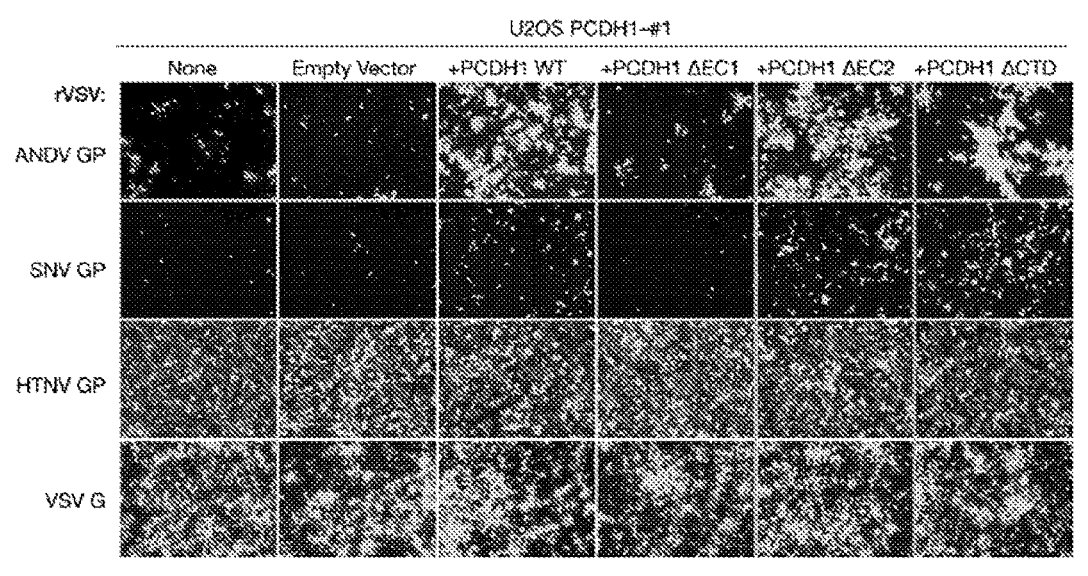
Figures 3B, 3C:
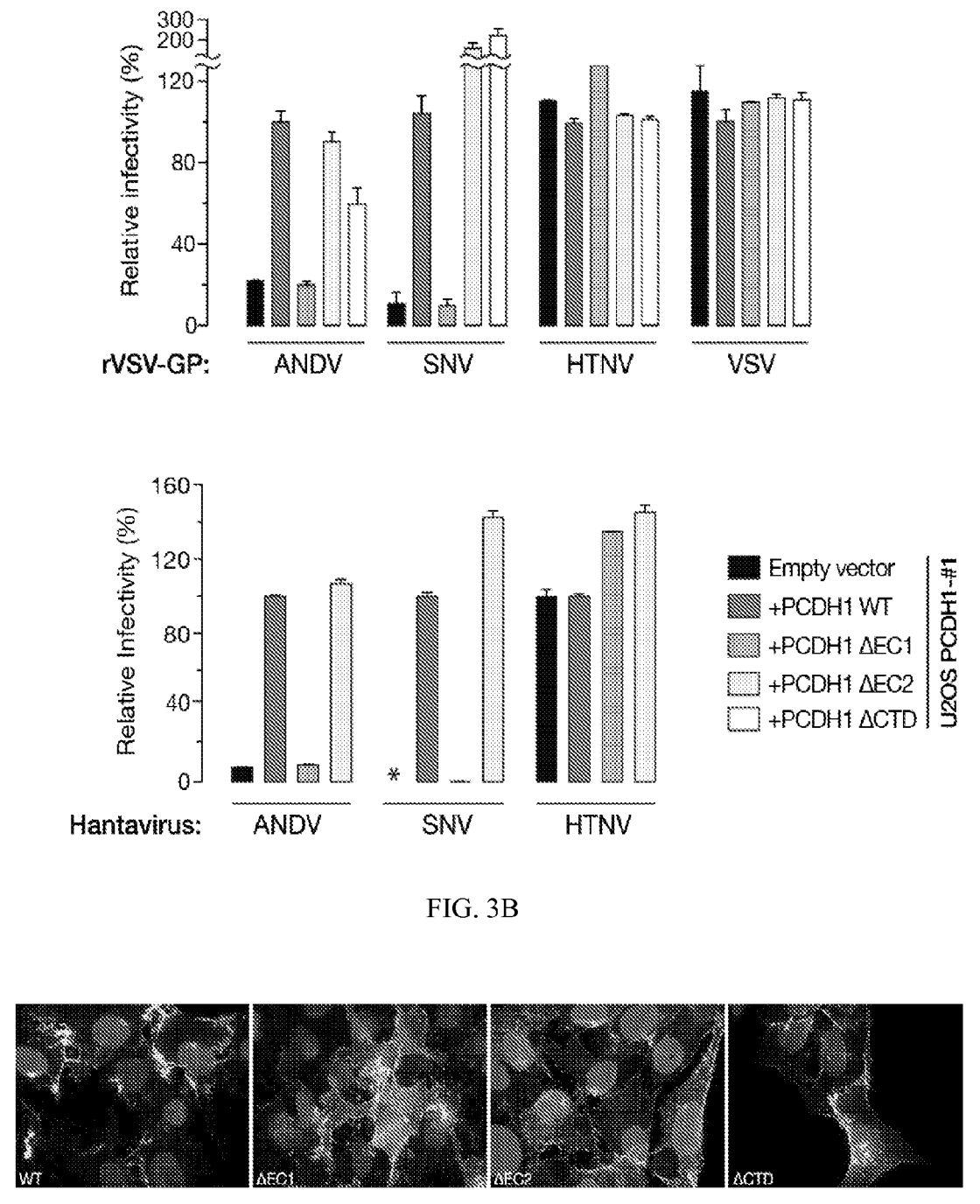
Figure 4:
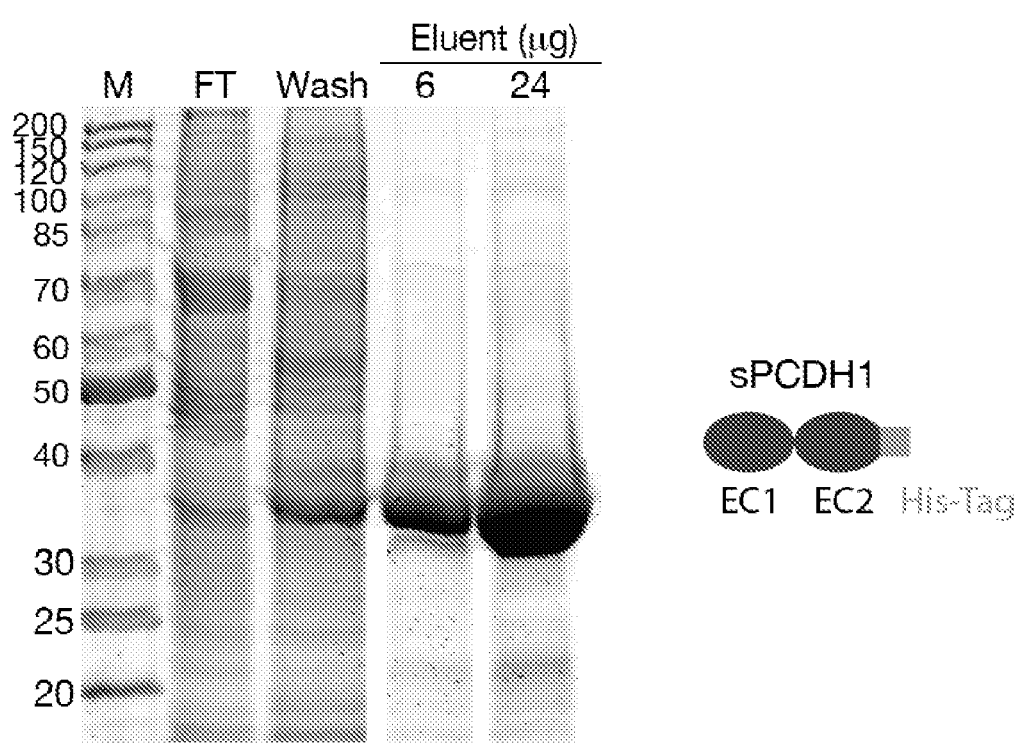
FIG. 4. Expression and purification of a soluble protein comprising the first and seond extracellular cadherin domains of human PCDH1 (sPCDH1-EC1/EC2). (Left) sPCDH1-EC1/EC2 bearing a C-terminal decahistidine tag was expressed in 293T human embryonic kidney cells and purifed from the supernatant by nickel-chelation chromatography. Proteins in the purification fractions were resolved by SDS-polyacrylamide gel electrophoresis and visualized by staining with Krypton Red infra-red staining. M—protein maker, FT—flowthrough.
Figure 5:
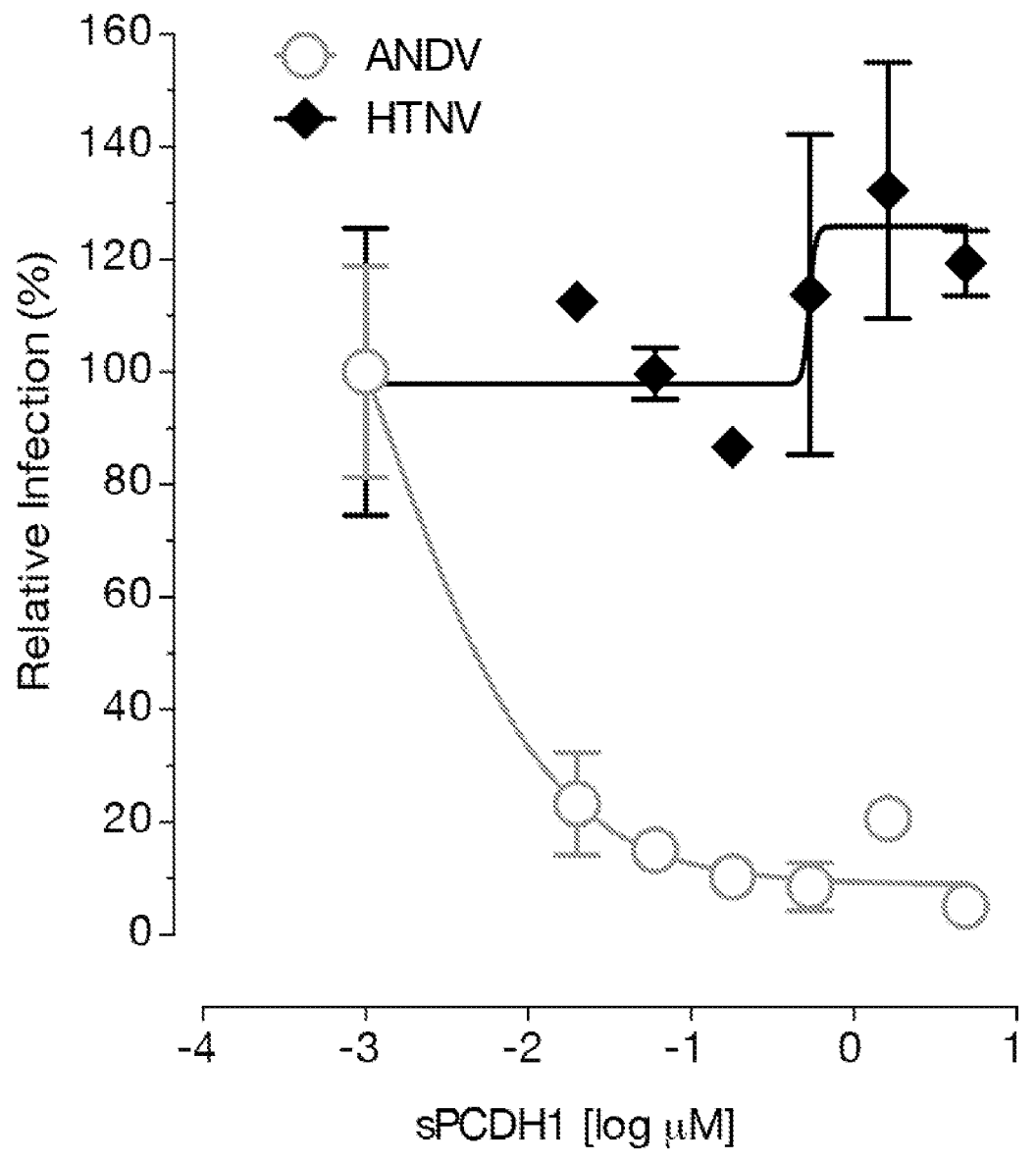
Figure 6:
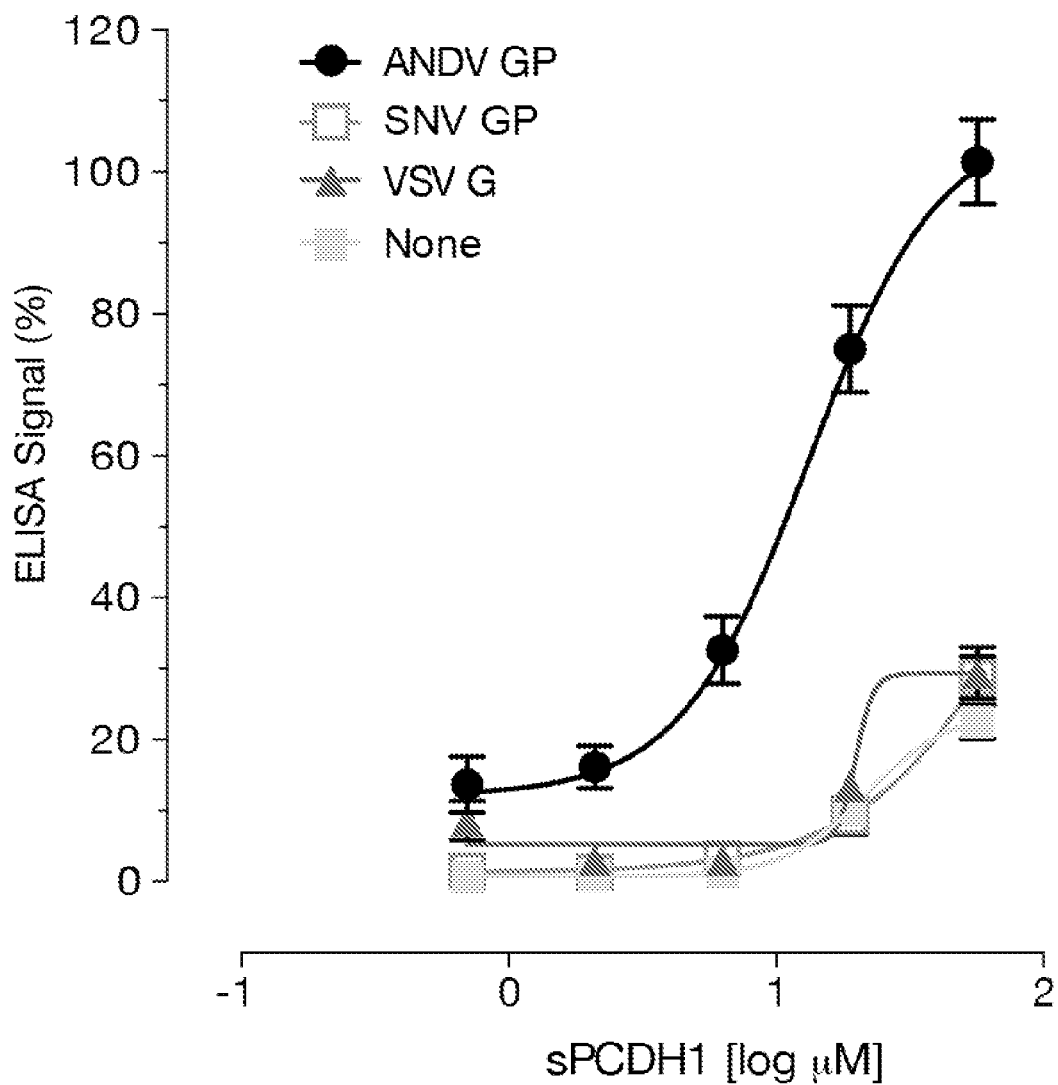
FIG. 6. ANDV GP can bind to sPCDH1-EC1/EC2 in vitro, but SNV GP and VSV G cannot. Magnetic beads coated with rVSVs bearing the indicated viral glycoproteins were incubated with increasing concentrations of sPCDH1-EC1/EC2, and binding of this protein was detected with an anti-flag antibody conjugated to horseradish peroxidase.

The PCDH1 protein is required for infection by the New World hantaviruses Andes virus (ANDV) and Sin Nombre virus (SNV), but not the Old World Hantaan virus (HTNV) hantavirus. This requirement was mapped to the first extracellular domain (EC1) of the PCDH1 as EC1 deletion reduces ANDV as well as SNV infections (FIG. 3A-B) without affecting expression and localization of the protein (FIG. 3C). Consistent with these findings, purified soluble PCDH1 protein containing the first two extracellular domains (sPCDH1-EC1/2, FIG. 4) blocked ANDV infection but not HTNV infection (FIG. 5). Soluble PCDH1 specifically binds to ANDV glycoprotein containing virions (FIG. 6) indicating that PCDH1 may be a receptor for the New World hantaviruses. Because infection by hantaviruses from the New World but not the Old World is associated with pulmonary disease, these results suggest that PCDH1 contributes to lung-specific infection and injury by hantaviruses.

Sequences and their features:

```
sPCDH1-EC1/EC2
                                                    (SEQ ID NO: 5)
MDSGAGGRRCPEAALLILGPPRMEHLRHSPGPGGQRLLLPSMLLALLLLLAPSPGHATRVV

YKVPEEQPPNTLIGSLAADYGFPDVGHLYKLEVGAPYLRVDGKTGDIFTTETSIDREGLRE

CQNQLPGDPCILEFEVSITDLVQNGSPRLLEGQIEVQDINDNTPNFASPVITLAIPENTNI

GSLFPIPLASDRDAGPNGVASYELQAGPEAQELFGLQVAEDQEEKQPQLIVMGNLDRERWD

SYDLTIKVQDGGSPPRASSALLRVTVLDTNDNAPKFERPSGSGHHHHHHHHHHTRPLEQKL

ISEEDLAANDILDYKDDDDKV

Features:
sPCDH1 signal peptide:    [1-57]
sPCDH1-EC1/EC2:           [58 : 280]
GSG Linker:               [285 : 287]
10-His:                   [288 : 297]
c-Myc tag:                [302 : 311]
Flag tag:                 [318 : 325]

PCDH1 Wild-type protein - 1060 amino acids
                                                    (SEQ ID NO: 4)
MDSGAGGRRCPEAALLILGPPRMEHLRHSPGPGGQRLLLPSMLLALLLLLAPSPGHATRVV

YKVPEEQPPNTLIGSLAADYGFPDVGHLYKLEVGAPYLRVDGKTGDIFTTETSIDREGLRE

CQNQLPGDPCILEFEVSITDLVQNGSPRLLEGQIEVQDINDNTPNFASPVITLAIPENTNI

GSLFPIPLASDRDAGPNGVASYELQAGPEAQELFGLQVAEDQEEKQPQLIVMGNLDRERWD

SYDLTIKVQDGGSPPRASSALLRVTVLDTNDNAPKFERPSYEAELSENSPIGHSVIQVKAN

DSDQGANAEIEYTFHQAPEVVRRLLRLDRNTGLITVQGPVDREDLSTLRFSVLAKDRGTNP

KSARAQVVVTVKDMNDNAPTIEIRGIGLVTHQDGMANISEDVAEETAVALVQVSDRDEGEN

AAVTCVVAGDVPFQLRQASETGSDSKKKYFLQTTTPLDYEKVKDYTIEIVAVDSGNPPLSS

TNSLKVQVVDVNDNAPVFTQSVTEVAFPENNKPGEVIAEITASDADSGSNAELVYSLEPEP

AAKGLFTISPETGEIQVKTSLDREQRESYELKVVAADRGSPSLQGTATVLVNVLDCNDNDP

KFMLSGYNFSVMENMPALSPVGMVTVIDGDKGENAQVQLSVEQDNGDFVIQNGTGTILSSL

SFDREQQSTYTFQLKAVDGGVPPRSAYVGVTINVLDENDNAPYITAPSNTSHKLLTPQTRL

GETVSQVAAEDFDSGVNAELIYSIAGGNPYGLFQIGSHSGAITLEKEIERRHHGLHRLVVK

VSDRGKPPRYGTALVHLYVNETLANRTLLETLLGHSLDTPLDIDIAGDPEYERSKQRGNIL

FGVVAGVVAVALLIALAVLVRYCRQREAKSGYQAGKKETKDLYAPKPSGKASKGNKSKGKK

SKSPKPVKPVEDEDEAGLQKSLKFNLMSDAPGDSPRIHLPLNYPPGSPDLGRHYRSNSPLP

SIQLQPQSPSASKKHQVVQDLPPANTFVGTGDTTSTGSEQYSDYSYRTNPPKYPSKQVGQP

FQLSTPQPLPHPYHGAIWTEVWE

Features:
sPCDH signal peptide:     [1-57]
EC1:                      [58 : 168]
EC2:                      [169 : 280]
CTD:                      [875 : 1060]
```

-continued

PCDH1 ΔEC1
(SEQ ID NO: 6)
MDSGAGGRRCPEAALLILGPPRMEHLRHSPGPGGQRLLLPSMLLALLLLLAPSPGHATRV<u>N
FASPVITLAIPENTNIGSLFPIPLASDRDAGPNGVASYELQAGPEAQELFGLQVAEDQEEK
QPQLIVMGNLDRERWDSYDLTIKVQDGGSPPRASSALLRVTVLDTNDNAPKF</u>ERPSYEAEL
SENSPIGHSVIQVKANDSDQGANAEIEYTFHQAPEVVRRLLRLDRNTGLITVQGPVDREDL
STLRFSVLAKDRGTNPKSARAQVVVTVKDMNDNAPTIEIRGIGLVTHQDGMANISEDVAEE
TAVALVQVSDRDEGENAAVTCVVAGDVPFQLRQASETGSDSKKKYFLQTTTPLDYEKVKDY
TIEIVAVDSGNPPLSSTNSLKVQVVDVNDNAPVFTQSVTEVAFPENNKPGEVIAEITASDA
DSGSNAELVYSLEPEPAAKGLFTISPETGEIQVKTSLDREQRESYELKVVAADRGSPSLQG
TATVLVNVLDCNDNDPKFMLSGYNFSVMENMPALSPVGMVTVIDGDKGENAQVQLSVEQDN
GDFVIQNGTGTILSSLSFDREQQSTYTFQLKAVDGGVPPRSAYVGVTINVLDENDNAPYIT
APSNTSHKLLTPQTRLGETVSQVAAEDFDSGVNAELIYSIAGGNPYGLFQIGSHSGAITLE
KEIERRHHGLHRLVVKVSDRGKPPRYGTALVHLYVNETLANRTLLETLLGHSLDTPLDIDI
AGDPEYERSKQRGNILFGVVAGVVAVALLIALAVLV<u>RYCRQREAKSGYQAGKKETKDLYAP
KPSGKASKGNKSKGKKSKSPKPVKPVEDEDEAGLQKSLKFNLMSDAPGDSPRIHLPLNYPP
GSPDLGRHYRSNSPLPSIQLQRQSPSASKKHQVVQDLPPANTFVGTGDTTSTGSEQYSDYS
YRTNPPKYPSKQVGQPFQLSTPQPLPHPYHGAIWTEVWE</u>

PCDH1 ΔEC2
(SEQ ID NO: 7)
MDSGAGGRRCPEAALLILGPPRMEHLRHSPGPGGQRLLLPSMLLALLLLLAPSPGHA**TRVV
YKVPEEQPPNTLIGSLAADYGFPDVGHLYKLEVGAPYLRVDGKTGDIFTTETSIDREGLRE
CQNQLPGDPCILEFEVSITDLVQNGSPRLLEGQIEVQDINDNTPNF**YEAELSENSPIGHSV
IQVKANDSDQGANAEIEYTFHQAPEVVRRLLRLDRNTGLITVQGPVDREDLSTLRFSVLAK
DRGTNPKSARAQVVVTVKDMNDNAPTIEIRGIGLVTHQDGMANISEDVAEETAVALVQVSD
RDEGENAAVTCVVAGDVPFQLRQASETGSDSKKKYFLQTTTPLDYEKVKDYTIEIVAVDSG
NPPLSSTNSLKVQVVDVNDNAPVFTQSVTEVAFPENNKPGEVIAEITASDADSGSNAELVY
SLEPEPAAKGLFTISPETGEIQVKTSLDREQRESYELKVVAADRGSPSLQGTATVLVNVLD
CNDNDPKFMLSGYNFSVMENMPALSPVGMVTVIDGDKGENAQVQLSVEQDNGDFVIQNGTG
TILSSLSFDREQQSTYTFQLKAVDGGVPPRSAYVGVTINVLDENDNAPYITAPSNTSHKLL
TPQTRLGETVSQVAAEDFDSGVNAELIYSIAGGNPYGLFQIGSHSGAITLEKEIERRHHGL
HRLVVKVSDRGKPPRYGTALVHLYVNETLANRTLLETLLGHSLDTPLDIDIAGDPEYERSK
QRGNILFGVVAGVVAVALLIALAVLV<u>RYCRQREAKSGYQAGKKETKDLYAPKPSGKASKGN
KSKGKKSKSPKPVKPVEDEDEAGLQKSLKFNLMSDAPGDSPRIHLPLNYPPGSPDLGRHYR
SNSPLPSIQLQPQSPSASKKHQVVQDLPPANTFVGTGDTTSTGSEQYSDYSYRTNPPKYPS
KQVGQPFQLSTPQPLPHPYHGAIWTEVWE</u>

Features:
sPCDH1 signal peptide:  [1-57]
EC1:                    [58 : 168]

PCDH1 ΔCTD
(SEQ ID NO: 8)
MDSGAGGRRCPEAALLILGPPRMEHLRHSPGPGGQRLLLPSMLLALLLLLAPSPGHA**TRVV
YKVPEEQPPNTLIGSLAADYGFPDVGHLYKLEVGAPYLRVDGKTGDIFTTETSIDREGLRE
CQNQLPGDPCILEFEVSITDLVQNGSPRLLEGQIEVQDINDNTPNF**<u>ASPVITLAIPENTNI</u>

-continued

GSLFPIPLASDRDAGPNGVASYELQAGPEAQELFGLQVAEDQEEKQPQLIVMGNLDRERWD

SYDLTIKVQDGGSPPRASSALLRVTVLDTNDNAPKFERPSYEAELSENSPIGHSVIQVKAN

DSDQGANAEIEYTFHQAPEVVRRLLRLDRNTGLITVQGPVDREDLSTLRFSVLAKDRGTNP

KSARAQVVVTVKDMNDNAPTIEIRGIGLVTHQDGMANISEDVAEETAVALVQVSDRDEGEN

AAVTCVVAGDVPFQLRQASETGSDSKKKYFLQTTTPLDYEKVKDYTIEIVAVDSGNPPLSS

TNSLKVQVVDVNDNAPVFTQSVTEVAFPENNKPGEVIAEITASDADSGSNAELVYSLEPEP

AAKGLFTISPETGEIQVKTSLDREQRESYELKVVAADRGSPSLQGTATVLVNVLDCNDNDP

KFMLSGYNFSVMENMPALSPVGMVTVIDGDKGENAQVQLSVEQDNGDFVIQNGTGTILSSL

SFDREQQSTYTFQLKAVDGGVPPRSAYVGVTINVLDENDNAPYITAPSNTSHKLLTPQTRL

GETVSQVAAEDFDSGVNAELIYSIAGGNPYGLFQIGSHSGAITLEKEIERRHHGLHRLVVK

VSDRGKPPRYGTALVHLYVNETLANRTLLETLLGHSLDTPLDIDIAGDPEYERSKQRGNIL

FGVVAGVVAVALLIALAVLV

Features:
sPCDH1 signal peptide:  [1-57]
EC1:                    [58 : 168]
EC2:                    [169 : 280]

Discussion

Protocadherin-1 is Expressed in Lung Tissue and is Genetically Implicated in Pulmonary Disease.

Andes virus (ANDV) and Sin Nombre virus (SNV) are respiratory pathogens that replicate in endothelial cells and macrophages in the lung and cause hantavirus pulmonary syndrome (HP S), which is characterized by pulmonary interstitial infiltrates and respiratory compromise, and clinically resembles acute respiratory distress syndrome (ARDS). Intriguingly, PCDH1 is genetically associated with bronchial hyperresponsiveness, a clinical hallmark of asthma (Koppelman et al., 2009), and with specific asthma subphenotypes (Toncheva et al., 2012; Mortensen et al., 2013). Consistent with its role in determining human susceptibility to airway disease, PCDH1 is expressed in airway epithelial cells and macrophages. These observations support the following: (1) PCDH1 is a lung-specific host factor for hantavirus infection; (2) the hantavirus-PCDH1 interaction may influence the course and severity of HPS; and (3) PCDH1 provides a therapeutic target for anti-hantavirus therapeutics to treat HPS.

REFERENCES

Carette, J. E., Raaben, M., Wong, A. C., Herbert, A. S., Obernosterer, G., Mulherkar, N., Kuehne, A. I., Kranzusch, P. J., Griffin, A. M., Ruthel, G., et al. (2011). Ebola virus entry requires the cholesterol transporter Niemann-Pick C1. Nature 477, 340-343.

Koppelman, G. H., Meyers, D. A., Howard, T. D., Zheng, S. L., Hawkins, G. A., Ampleford, E. J., Xu, J., Koning, H., Bruinenberg, M., Nolte, I. M., et al. (2009). Identification of PCDH1 as a novel susceptibility gene for bronchial hyperresponsiveness. Am. J. Respir. Crit. Care Med. 180, 929-935.

Mortensen, L. J., Kreiner-Moller, E., Hakonarson, H., Bøonnelykke, K., and Bisgaard, H. (2013). The PCDH1-gene and asthma in early childhood. Eur. Respir. J. In press. PMID: 23988763.

Toncheva A. A, Suttner K, Michel S, Klopp N, Illig T, Balschun T, Vogelberg C, von Berg A, Bufe A, Heinzmann A, Laub O, Rietschel E, Simma B, Frischer T, Genuneit J, von Mutius E, Kabesch M. (2012). Genetic variants in Protocadherin-1, bronchial hyper-responsiveness, and asthma subphenotypes in German children. Pediatric Allergy Immu 23, 636-641.

What is claimed is:

1. A method of binding protocadherin-1 (PCDH1) in a subject infected with a New World hantavirus or a subject at risk for infection with a New World hantavirus comprising administering to the subject an antibody or antibody fragment that binds to PCDH1.

2. The method of claim 1, wherein the New World hantavirus is one or more of Sin Nombre virus (SNV), Andes virus (ANDV), New York Virus and Black Creek Canal Virus.

3. The method of claim 1, wherein the subject infected with the New World hantavirus has one or more of hantavirus pulmonary syndrome (HPS), hemorrhagic fever with renal syndrome (HFRS), and nephropathia epidemica (NE).

4. The method of claim 1, wherein the subject at risk for infection with a New World hantavirus is exposed to a New World hantavirus as the result of bioterrorism or biological warfare.

5. The method of claim 1, wherein the subject at risk for infection with a New World hantavirus is a first responder, medical or military personnel, a biosafety level ¾ personnel or an animal worker.

6. The method of claim 1, wherein the antibody or antibody fragment prevents entry of the New World hantavirus into cells of a subject.

7. The method of claim 1, wherein the antibody is a monoclonal antibody.

8. The method of claim 1, wherein the antibody or antibody fragment agent binds to the first extra-cellular domain (EC1) of PCDH1.

* * * * *

SEQUENCE LISTING

<160> NUMBER OF SEQ ID NOS: 8

<210> SEQ ID NO 1
<211> LENGTH: 43
<212> TYPE: DNA
<213> ORGANISM: Homo sapiens

<400> SEQUENCE: 1
acgcccccaa gtttgagcgg ccctcctatg aggccgaact atc        43

<210> SEQ ID NO 2
<211> LENGTH: 39
<212> TYPE: DNA

-continued

<213> ORGANISM: Homo sapiens

<400> SEQUENCE: 2
acgcccccaa gtttgagcgg ccctcctatg aggccgaac                39

<210> SEQ ID NO 3
<211> LENGTH: 30
<212> TYPE: DNA
<213> ORGANISM: Homo sapiens

<400> SEQUENCE: 3
acgcccccaa gtttgagcgg ccctcctatg                          30

<210> SEQ ID NO 4
<211> LENGTH: 1060
<212> TYPE: PRT
<213> ORGANISM: Homo sapiens

<400> SEQUENCE: 4

```
Met Asp Ser Gly Ala Gly Gly Arg Arg Cys Pro Glu Ala Ala Leu Leu
1               5                   10                  15

Ile Leu Gly Pro Pro Arg Met Glu His Leu Arg His Ser Pro Gly Pro
            20                  25                  30

Gly Gly Gln Arg Leu Leu Leu Pro Ser Met Leu Leu Ala Leu Leu Leu
        35                  40                  45

Leu Leu Ala Pro Ser Pro Gly His Ala Thr Arg Val Val Tyr Lys Val
    50                  55                  60

Pro Glu Glu Gln Pro Pro Asn Thr Leu Ile Gly Ser Leu Ala Ala Asp
65                  70                  75                  80

Tyr Gly Phe Pro Asp Val Gly His Leu Tyr Lys Leu Glu Val Gly Ala
                85                  90                  95

Pro Tyr Leu Arg Val Asp Gly Lys Thr Gly Asp Ile Phe Thr Thr Glu
            100                 105                 110

Thr Ser Ile Asp Arg Glu Gly Leu Arg Glu Cys Gln Asn Gln Leu Pro
        115                 120                 125

Gly Asp Pro Cys Ile Leu Glu Phe Glu Val Ser Ile Thr Asp Leu Val
    130                 135                 140

Gln Asn Gly Ser Pro Arg Leu Leu Glu Gly Gln Ile Glu Val Gln Asp
145                 150                 155                 160

Ile Asn Asp Asn Thr Pro Asn Phe Ala Ser Pro Val Ile Thr Leu Ala
                165                 170                 175

Ile Pro Glu Asn Thr Asn Ile Gly Ser Leu Phe Pro Ile Pro Leu Ala
            180                 185                 190

Ser Asp Arg Asp Ala Gly Pro Asn Gly Val Ala Ser Tyr Glu Leu Gln
        195                 200                 205

Ala Gly Pro Glu Ala Gln Glu Leu Phe Gly Leu Gln Val Ala Glu Asp
    210                 215                 220

Gln Glu Glu Lys Gln Pro Gln Leu Ile Val Met Gly Asn Leu Asp Arg
225                 230                 235                 240

Glu Arg Trp Asp Ser Tyr Asp Leu Thr Ile Lys Val Gln Asp Gly Gly
                245                 250                 255

Ser Pro Pro Arg Ala Ser Ser Ala Leu Leu Arg Val Thr Val Leu Asp
            260                 265                 270

Thr Asn Asp Asn Ala Pro Lys Phe Glu Arg Pro Ser Tyr Glu Ala Glu
        275                 280                 285

Leu Ser Glu Asn Ser Pro Ile Gly His Ser Val Ile Gln Val Lys Ala
```

```
                290                 295                 300
Asn Asp Ser Asp Gln Gly Ala Asn Ala Glu Ile Glu Tyr Thr Phe His
305                 310                 315                 320

Gln Ala Pro Glu Val Val Arg Leu Leu Arg Leu Asp Arg Asn Thr
                325                 330                 335

Gly Leu Ile Thr Val Gln Gly Pro Val Asp Arg Glu Asp Leu Ser Thr
                340                 345                 350

Leu Arg Phe Ser Val Leu Ala Lys Asp Arg Gly Thr Asn Pro Lys Ser
                355                 360                 365

Ala Arg Ala Gln Val Val Thr Val Lys Asp Met Asn Asp Asn Ala
                370                 375                 380

Pro Thr Ile Glu Ile Arg Gly Ile Gly Leu Val Thr His Gln Asp Gly
385                 390                 395                 400

Met Ala Asn Ile Ser Glu Asp Val Ala Glu Thr Ala Val Ala Leu
                405                 410                 415

Val Gln Val Ser Asp Arg Asp Glu Gly Glu Asn Ala Ala Val Thr Cys
                420                 425                 430

Val Val Ala Gly Asp Val Pro Phe Gln Leu Arg Gln Ala Ser Glu Thr
                435                 440                 445

Gly Ser Asp Ser Lys Lys Lys Tyr Phe Leu Gln Thr Thr Thr Pro Leu
450                 455                 460

Asp Tyr Glu Lys Val Lys Asp Tyr Thr Ile Glu Ile Val Ala Val Asp
465                 470                 475                 480

Ser Gly Asn Pro Pro Leu Ser Ser Thr Asn Ser Leu Lys Val Gln Val
                485                 490                 495

Val Asp Val Asn Asp Asn Ala Pro Val Phe Thr Gln Ser Val Thr Glu
                500                 505                 510

Val Ala Phe Pro Glu Asn Asn Lys Pro Gly Glu Val Ile Ala Glu Ile
                515                 520                 525

Thr Ala Ser Asp Ala Asp Ser Gly Ser Asn Ala Glu Leu Val Tyr Ser
                530                 535                 540

Leu Glu Pro Glu Pro Ala Ala Lys Gly Leu Phe Thr Ile Ser Pro Glu
545                 550                 555                 560

Thr Gly Glu Ile Gln Val Lys Thr Ser Leu Asp Arg Glu Gln Arg Glu
                565                 570                 575

Ser Tyr Glu Leu Lys Val Ala Ala Asp Arg Gly Ser Pro Ser Leu
                580                 585                 590

Gln Gly Thr Ala Thr Val Leu Val Asn Val Leu Asp Cys Asn Asp Asn
                595                 600                 605

Asp Pro Lys Phe Met Leu Ser Gly Tyr Asn Phe Ser Val Met Glu Asn
                610                 615                 620

Met Pro Ala Leu Ser Pro Val Gly Met Val Thr Val Ile Asp Gly Asp
625                 630                 635                 640

Lys Gly Glu Asn Ala Gln Val Gln Leu Ser Val Glu Gln Asp Asn Gly
                645                 650                 655

Asp Phe Val Ile Gln Asn Gly Thr Gly Thr Ile Leu Ser Ser Leu Ser
                660                 665                 670

Phe Asp Arg Glu Gln Gln Ser Thr Tyr Thr Phe Gln Leu Lys Ala Val
                675                 680                 685

Asp Gly Gly Val Pro Pro Arg Ser Ala Tyr Val Gly Val Thr Ile Asn
                690                 695                 700

Val Leu Asp Glu Asn Asp Asn Ala Pro Tyr Ile Thr Ala Pro Ser Asn
705                 710                 715                 720
```

Thr Ser His Lys Leu Leu Thr Pro Gln Thr Arg Leu Gly Glu Thr Val
            725                 730                 735

Ser Gln Val Ala Ala Glu Asp Phe Asp Ser Gly Val Asn Ala Glu Leu
            740                 745                 750

Ile Tyr Ser Ile Ala Gly Gly Asn Pro Tyr Gly Leu Phe Gln Ile Gly
            755                 760                 765

Ser His Ser Gly Ala Ile Thr Leu Glu Lys Glu Ile Glu Arg Arg His
            770                 775                 780

His Gly Leu His Arg Leu Val Val Lys Val Ser Asp Arg Gly Lys Pro
785                 790                 795                 800

Pro Arg Tyr Gly Thr Ala Leu Val His Leu Tyr Val Asn Glu Thr Leu
            805                 810                 815

Ala Asn Arg Thr Leu Leu Glu Thr Leu Leu Gly His Ser Leu Asp Thr
            820                 825                 830

Pro Leu Asp Ile Asp Ile Ala Gly Asp Pro Glu Tyr Glu Arg Ser Lys
            835                 840                 845

Gln Arg Gly Asn Ile Leu Phe Gly Val Val Ala Gly Val Val Ala Val
            850                 855                 860

Ala Leu Leu Ile Ala Leu Ala Val Leu Val Arg Tyr Cys Arg Gln Arg
865                 870                 875                 880

Glu Ala Lys Ser Gly Tyr Gln Ala Gly Lys Lys Glu Thr Lys Asp Leu
            885                 890                 895

Tyr Ala Pro Lys Pro Ser Gly Lys Ala Ser Lys Gly Asn Lys Ser Lys
            900                 905                 910

Gly Lys Lys Ser Lys Ser Pro Lys Pro Val Lys Pro Val Glu Asp Glu
            915                 920                 925

Asp Glu Ala Gly Leu Gln Lys Ser Leu Lys Phe Asn Leu Met Ser Asp
930                 935                 940

Ala Pro Gly Asp Ser Pro Arg Ile His Leu Pro Leu Asn Tyr Pro Pro
945                 950                 955                 960

Gly Ser Pro Asp Leu Gly Arg His Tyr Arg Ser Asn Ser Pro Leu Pro
            965                 970                 975

Ser Ile Gln Leu Gln Pro Gln Ser Pro Ser Ala Ser Lys Lys His Gln
            980                 985                 990

Val Val Gln Asp Leu Pro Pro Ala Asn Thr Phe Val Gly Thr Gly Asp
            995                 1000                1005

Thr Thr Ser Thr Gly Ser Glu Gln Tyr Ser Asp Tyr Ser Tyr Arg
        1010                1015                1020

Thr Asn Pro Pro Lys Tyr Pro Ser Lys Gln Val Gly Gln Pro Phe
        1025                1030                1035

Gln Leu Ser Thr Pro Gln Pro Leu Pro His Pro Tyr His Gly Ala
        1040                1045                1050

Ile Trp Thr Glu Val Trp Glu
        1055                1060

<210> SEQ ID NO 5
<211> LENGTH: 326
<212> TYPE: PRT
<213> ORGANISM: Homo sapiens

<400> SEQUENCE: 5

Met Asp Ser Gly Ala Gly Gly Arg Arg Cys Pro Glu Ala Ala Leu Leu
1               5                   10                  15

Ile Leu Gly Pro Pro Arg Met Glu His Leu Arg His Ser Pro Gly Pro

```
                    20                  25                  30
Gly Gly Gln Arg Leu Leu Leu Pro Ser Met Leu Leu Ala Leu Leu Leu
            35                  40                  45

Leu Leu Ala Pro Ser Pro Gly His Ala Thr Arg Val Val Tyr Lys Val
50                  55                  60

Pro Glu Glu Gln Pro Pro Asn Thr Leu Ile Gly Ser Leu Ala Ala Asp
65                  70                  75                  80

Tyr Gly Phe Pro Asp Val Gly His Leu Tyr Lys Leu Glu Val Gly Ala
                85                  90                  95

Pro Tyr Leu Arg Val Asp Gly Lys Thr Gly Asp Ile Phe Thr Thr Glu
            100                 105                 110

Thr Ser Ile Asp Arg Glu Gly Leu Arg Glu Cys Gln Asn Gln Leu Pro
        115                 120                 125

Gly Asp Pro Cys Ile Leu Glu Phe Glu Val Ser Ile Thr Asp Leu Val
    130                 135                 140

Gln Asn Gly Ser Pro Arg Leu Leu Glu Gly Gln Ile Glu Val Gln Asp
145                 150                 155                 160

Ile Asn Asp Asn Thr Pro Asn Phe Ala Ser Pro Val Ile Thr Leu Ala
                165                 170                 175

Ile Pro Glu Asn Thr Asn Ile Gly Ser Leu Phe Pro Ile Pro Leu Ala
            180                 185                 190

Ser Asp Arg Asp Ala Gly Pro Asn Gly Val Ala Ser Tyr Glu Leu Gln
        195                 200                 205

Ala Gly Pro Glu Ala Gln Glu Leu Phe Gly Leu Gln Val Ala Glu Asp
    210                 215                 220

Gln Glu Glu Lys Gln Pro Gln Leu Ile Val Met Gly Asn Leu Asp Arg
225                 230                 235                 240

Glu Arg Trp Asp Ser Tyr Asp Leu Thr Ile Lys Val Gln Asp Gly Gly
                245                 250                 255

Ser Pro Pro Arg Ala Ser Ser Ala Leu Leu Arg Val Thr Val Leu Asp
            260                 265                 270

Thr Asn Asp Asn Ala Pro Lys Phe Glu Arg Pro Ser Gly Ser Gly His
        275                 280                 285

His His His His His His His Thr Arg Pro Leu Glu Gln Lys
    290                 295                 300

Leu Ile Ser Glu Glu Asp Leu Ala Ala Asn Asp Ile Leu Asp Tyr Lys
305                 310                 315                 320

Asp Asp Asp Asp Lys Val
                325

<210> SEQ ID NO 6
<211> LENGTH: 954
<212> TYPE: PRT
<213> ORGANISM: Homo sapiens

<400> SEQUENCE: 6

Met Asp Ser Gly Ala Gly Gly Arg Arg Cys Pro Glu Ala Ala Leu Leu
1               5                   10                  15

Ile Leu Gly Pro Pro Arg Met Glu His Leu Arg His Ser Pro Gly Pro
            20                  25                  30

Gly Gly Gln Arg Leu Leu Leu Pro Ser Met Leu Leu Ala Leu Leu Leu
        35                  40                  45

Leu Leu Ala Pro Ser Pro Gly His Ala Thr Arg Val Asn Phe Ala Ser
    50                  55                  60
```

-continued

```
Pro Val Ile Thr Leu Ala Ile Pro Glu Asn Thr Asn Ile Gly Ser Leu
 65                  70                  75                  80

Phe Pro Ile Pro Leu Ala Ser Asp Arg Asp Ala Gly Pro Asn Gly Val
                 85                  90                  95

Ala Ser Tyr Glu Leu Gln Ala Gly Pro Glu Ala Gln Glu Leu Phe Gly
            100                 105                 110

Leu Gln Val Ala Glu Asp Gln Glu Lys Gln Pro Gln Leu Ile Val
        115                 120                 125

Met Gly Asn Leu Asp Arg Glu Arg Trp Asp Ser Tyr Asp Leu Thr Ile
    130                 135                 140

Lys Val Gln Asp Gly Gly Ser Pro Pro Arg Ala Ser Ser Ala Leu Leu
145                 150                 155                 160

Arg Val Thr Val Leu Asp Thr Asn Asp Asn Ala Pro Lys Phe Glu Arg
                165                 170                 175

Pro Ser Tyr Glu Ala Glu Leu Ser Glu Asn Ser Pro Ile Gly His Ser
            180                 185                 190

Val Ile Gln Val Lys Ala Asn Asp Ser Asp Gln Gly Ala Asn Ala Glu
        195                 200                 205

Ile Glu Tyr Thr Phe His Gln Ala Pro Glu Val Val Arg Arg Leu Leu
    210                 215                 220

Arg Leu Asp Arg Asn Thr Gly Leu Ile Thr Val Gln Gly Pro Val Asp
225                 230                 235                 240

Arg Glu Asp Leu Ser Thr Leu Arg Phe Ser Val Leu Ala Lys Asp Arg
                245                 250                 255

Gly Thr Asn Pro Lys Ser Ala Arg Ala Gln Val Val Thr Val Lys
            260                 265                 270

Asp Met Asn Asp Asn Ala Pro Thr Ile Glu Ile Arg Gly Ile Gly Leu
        275                 280                 285

Val Thr His Gln Asp Gly Met Ala Asn Ile Ser Glu Asp Val Ala Glu
    290                 295                 300

Glu Thr Ala Val Ala Leu Val Gln Val Ser Asp Arg Asp Glu Gly Glu
305                 310                 315                 320

Asn Ala Ala Val Thr Cys Val Val Ala Gly Asp Val Pro Phe Gln Leu
                325                 330                 335

Arg Gln Ala Ser Glu Thr Gly Ser Asp Ser Lys Lys Lys Tyr Phe Leu
            340                 345                 350

Gln Thr Thr Thr Pro Leu Asp Tyr Glu Lys Val Lys Asp Tyr Thr Ile
        355                 360                 365

Glu Ile Val Ala Val Asp Ser Gly Asn Pro Pro Leu Ser Ser Thr Asn
    370                 375                 380

Ser Leu Lys Val Gln Val Val Asp Val Asn Asp Asn Ala Pro Val Phe
385                 390                 395                 400

Thr Gln Ser Val Thr Glu Val Ala Phe Pro Glu Asn Asn Lys Pro Gly
                405                 410                 415

Glu Val Ile Ala Glu Ile Thr Ala Ser Asp Ala Asp Ser Gly Ser Asn
            420                 425                 430

Ala Glu Leu Val Tyr Ser Leu Glu Pro Glu Pro Ala Ala Lys Gly Leu
        435                 440                 445

Phe Thr Ile Ser Pro Glu Thr Gly Glu Ile Gln Val Lys Thr Ser Leu
    450                 455                 460

Asp Arg Glu Gln Arg Glu Ser Tyr Glu Leu Lys Val Val Ala Ala Asp
465                 470                 475                 480

Arg Gly Ser Pro Ser Leu Gln Gly Thr Ala Thr Val Leu Val Asn Val
```

```
                    485             490                 495
Leu Asp Cys Asn Asp Asn Asp Pro Lys Phe Met Leu Ser Gly Tyr Asn
                500             505             510

Phe Ser Val Met Glu Asn Met Pro Ala Leu Ser Pro Val Gly Met Val
            515             520             525

Thr Val Ile Asp Gly Asp Lys Gly Glu Asn Ala Gln Val Gln Leu Ser
        530             535             540

Val Glu Gln Asp Asn Gly Asp Phe Val Ile Gln Asn Gly Thr Gly Thr
545             550             555             560

Ile Leu Ser Ser Leu Ser Phe Asp Arg Glu Gln Gln Ser Thr Tyr Thr
            565             570             575

Phe Gln Leu Lys Ala Val Asp Gly Gly Val Pro Pro Arg Ser Ala Tyr
            580             585             590

Val Gly Val Thr Ile Asn Val Leu Asp Glu Asn Asp Asn Ala Pro Tyr
        595             600             605

Ile Thr Ala Pro Ser Asn Thr Ser His Lys Leu Leu Thr Pro Gln Thr
        610             615             620

Arg Leu Gly Glu Thr Val Ser Gln Val Ala Ala Glu Asp Phe Asp Ser
625             630             635             640

Gly Val Asn Ala Glu Leu Ile Tyr Ser Ile Ala Gly Gly Asn Pro Tyr
                645             650             655

Gly Leu Phe Gln Ile Gly Ser His Ser Gly Ala Ile Thr Leu Glu Lys
            660             665             670

Glu Ile Glu Arg Arg His His Gly Leu His Arg Leu Val Val Lys Val
            675             680             685

Ser Asp Arg Gly Lys Pro Pro Arg Tyr Gly Thr Ala Leu Val His Leu
690             695             700

Tyr Val Asn Glu Thr Leu Ala Asn Arg Thr Leu Leu Glu Thr Leu Leu
705             710             715             720

Gly His Ser Leu Asp Thr Pro Leu Asp Ile Asp Ile Ala Gly Asp Pro
            725             730             735

Glu Tyr Glu Arg Ser Lys Gln Arg Gly Asn Ile Leu Phe Gly Val Val
            740             745             750

Ala Gly Val Val Ala Val Ala Leu Leu Ile Ala Leu Ala Val Leu Val
        755             760             765

Arg Tyr Cys Arg Gln Arg Glu Ala Lys Ser Gly Tyr Gln Ala Gly Lys
        770             775             780

Lys Glu Thr Lys Asp Leu Tyr Ala Pro Lys Pro Ser Gly Lys Ala Ser
785             790             795             800

Lys Gly Asn Lys Ser Lys Gly Lys Lys Ser Lys Ser Pro Lys Pro Val
            805             810             815

Lys Pro Val Glu Asp Glu Asp Glu Ala Gly Leu Gln Lys Ser Leu Lys
            820             825             830

Phe Asn Leu Met Ser Asp Ala Pro Gly Asp Ser Pro Arg Ile His Leu
        835             840             845

Pro Leu Asn Tyr Pro Pro Gly Ser Pro Asp Leu Gly Arg His Tyr Arg
        850             855             860

Ser Asn Ser Pro Leu Pro Ser Ile Gln Leu Gln Pro Gln Ser Pro Ser
865             870             875             880

Ala Ser Lys Lys His Gln Val Val Gln Asp Leu Pro Pro Ala Asn Thr
            885             890             895

Phe Val Gly Thr Gly Asp Thr Thr Ser Thr Gly Ser Glu Gln Tyr Ser
            900             905             910
```

Asp Tyr Ser Tyr Arg Thr Asn Pro Pro Lys Tyr Pro Ser Lys Gln Val
        915                 920                 925

Gly Gln Pro Phe Gln Leu Ser Thr Pro Gln Pro Leu Pro His Pro Tyr
930                 935                 940

His Gly Ala Ile Trp Thr Glu Val Trp Glu
945                 950

<210> SEQ ID NO 7
<211> LENGTH: 944
<212> TYPE: PRT
<213> ORGANISM: Homo sapiens

<400> SEQUENCE: 7

Met Asp Ser Gly Ala Gly Gly Arg Arg Cys Pro Glu Ala Ala Leu Leu
1               5                   10                  15

Ile Leu Gly Pro Pro Arg Met Glu His Leu Arg His Ser Pro Gly Pro
                20                  25                  30

Gly Gly Gln Arg Leu Leu Leu Pro Ser Met Leu Leu Ala Leu Leu Leu
            35                  40                  45

Leu Leu Ala Pro Ser Pro Gly His Ala Thr Arg Val Val Tyr Lys Val
        50                  55                  60

Pro Glu Glu Gln Pro Pro Asn Thr Leu Ile Gly Ser Leu Ala Ala Asp
65                  70                  75                  80

Tyr Gly Phe Pro Asp Val Gly His Leu Tyr Lys Leu Glu Val Gly Ala
                85                  90                  95

Pro Tyr Leu Arg Val Asp Gly Lys Thr Gly Asp Ile Phe Thr Thr Glu
            100                 105                 110

Thr Ser Ile Asp Arg Glu Gly Leu Arg Glu Cys Gln Asn Gln Leu Pro
        115                 120                 125

Gly Asp Pro Cys Ile Leu Glu Phe Glu Val Ser Ile Thr Asp Leu Val
130                 135                 140

Gln Asn Gly Ser Pro Arg Leu Leu Glu Gly Gln Ile Glu Val Gln Asp
145                 150                 155                 160

Ile Asn Asp Asn Thr Pro Asn Phe Tyr Glu Ala Glu Leu Ser Glu Asn
                165                 170                 175

Ser Pro Ile Gly His Ser Val Ile Gln Val Lys Ala Asn Asp Ser Asp
            180                 185                 190

Gln Gly Ala Asn Ala Glu Ile Glu Tyr Thr Phe His Gln Ala Pro Glu
        195                 200                 205

Val Val Arg Arg Leu Leu Arg Leu Asp Arg Asn Thr Gly Leu Ile Thr
    210                 215                 220

Val Gln Gly Pro Val Asp Arg Glu Asp Leu Ser Thr Leu Arg Phe Ser
225                 230                 235                 240

Val Leu Ala Lys Asp Arg Gly Thr Asn Pro Lys Ser Ala Arg Ala Gln
                245                 250                 255

Val Val Val Thr Val Lys Asp Met Asn Asp Asn Ala Pro Thr Ile Glu
            260                 265                 270

Ile Arg Gly Ile Gly Leu Val Thr His Gln Asp Gly Met Ala Asn Ile
        275                 280                 285

Ser Glu Asp Val Ala Glu Thr Ala Val Ala Leu Val Gln Val Ser
    290                 295                 300

Asp Arg Asp Glu Gly Glu Asn Ala Ala Val Thr Cys Val Val Ala Gly
305                 310                 315                 320

Asp Val Pro Phe Gln Leu Arg Gln Ala Ser Glu Thr Gly Ser Asp Ser

```
            325                 330                 335
Lys Lys Lys Tyr Phe Leu Gln Thr Thr Thr Pro Leu Asp Tyr Glu Lys
            340                 345                 350

Val Lys Asp Tyr Thr Ile Glu Ile Val Ala Val Asp Ser Gly Asn Pro
            355                 360                 365

Pro Leu Ser Ser Thr Asn Ser Leu Lys Val Gln Val Asp Val Asn
            370                 375                 380

Asp Asn Ala Pro Val Phe Thr Gln Ser Val Thr Glu Val Ala Phe Pro
385                 390                 395                 400

Glu Asn Asn Lys Pro Gly Glu Val Ile Ala Glu Ile Thr Ala Ser Asp
                    405                 410                 415

Ala Asp Ser Gly Ser Asn Ala Glu Leu Val Tyr Ser Leu Glu Pro Glu
                420                 425                 430

Pro Ala Ala Lys Gly Leu Phe Thr Ile Ser Pro Glu Thr Gly Glu Ile
                435                 440                 445

Gln Val Lys Thr Ser Leu Asp Arg Glu Gln Arg Glu Ser Tyr Glu Leu
            450                 455                 460

Lys Val Ala Ala Asp Arg Gly Ser Pro Ser Leu Gln Gly Thr Ala
465                 470                 475                 480

Thr Val Leu Val Asn Val Leu Asp Cys Asn Asp Asn Pro Lys Phe
                    485                 490                 495

Met Leu Ser Gly Tyr Asn Phe Ser Val Met Glu Asn Met Pro Ala Leu
                500                 505                 510

Ser Pro Val Gly Met Val Thr Val Ile Asp Gly Asp Lys Gly Glu Asn
                515                 520                 525

Ala Gln Val Gln Leu Ser Val Glu Gln Asp Asn Gly Asp Phe Val Ile
            530                 535                 540

Gln Asn Gly Thr Gly Thr Ile Leu Ser Ser Leu Ser Phe Asp Arg Glu
545                 550                 555                 560

Gln Gln Ser Thr Tyr Thr Phe Gln Leu Lys Ala Val Asp Gly Gly Val
                565                 570                 575

Pro Pro Arg Ser Ala Tyr Val Gly Val Thr Ile Asn Val Leu Asp Glu
                580                 585                 590

Asn Asp Asn Ala Pro Tyr Ile Thr Ala Pro Ser Asn Thr Ser His Lys
                595                 600                 605

Leu Leu Thr Pro Gln Thr Arg Leu Gly Glu Thr Val Ser Gln Val Ala
            610                 615                 620

Ala Glu Asp Phe Asp Ser Gly Val Asn Ala Glu Leu Ile Tyr Ser Ile
625                 630                 635                 640

Ala Gly Gly Asn Pro Tyr Gly Leu Phe Gln Ile Gly Ser His Ser Gly
                645                 650                 655

Ala Ile Thr Leu Glu Lys Glu Ile Glu Arg Arg His His Gly Leu His
                660                 665                 670

Arg Leu Val Val Lys Val Ser Asp Arg Gly Lys Pro Pro Arg Tyr Gly
            675                 680                 685

Thr Ala Leu Val His Leu Tyr Val Asn Glu Thr Leu Ala Asn Arg Thr
            690                 695                 700

Leu Leu Glu Thr Leu Leu Gly His Ser Leu Asp Thr Pro Leu Asp Ile
705                 710                 715                 720

Asp Ile Ala Gly Asp Pro Glu Tyr Glu Arg Ser Lys Gln Arg Gly Asn
                725                 730                 735

Ile Leu Phe Gly Val Val Ala Gly Val Val Ala Val Ala Leu Leu Ile
                740                 745                 750
```

```
Ala Leu Ala Val Leu Val Arg Tyr Cys Arg Gln Arg Glu Ala Lys Ser
        755                 760                 765

Gly Tyr Gln Ala Gly Lys Lys Glu Thr Lys Asp Leu Tyr Ala Pro Lys
    770                 775                 780

Pro Ser Gly Lys Ala Ser Lys Gly Asn Lys Ser Lys Gly Lys Lys Ser
785                 790                 795                 800

Lys Ser Pro Lys Pro Val Lys Pro Val Glu Asp Glu Asp Glu Ala Gly
                805                 810                 815

Leu Gln Lys Ser Leu Lys Phe Asn Leu Met Ser Asp Ala Pro Gly Asp
            820                 825                 830

Ser Pro Arg Ile His Leu Pro Leu Asn Tyr Pro Gly Ser Pro Asp
        835                 840                 845

Leu Gly Arg His Tyr Arg Ser Asn Ser Pro Leu Pro Ser Ile Gln Leu
        850                 855                 860

Gln Pro Gln Ser Pro Ser Ala Ser Lys Lys His Gln Val Val Gln Asp
865                 870                 875                 880

Leu Pro Pro Ala Asn Thr Phe Val Gly Thr Gly Asp Thr Thr Ser Thr
                885                 890                 895

Gly Ser Glu Gln Tyr Ser Asp Tyr Ser Tyr Arg Thr Asn Pro Pro Lys
            900                 905                 910

Tyr Pro Ser Lys Gln Val Gly Gln Pro Phe Gln Leu Ser Thr Pro Gln
        915                 920                 925

Pro Leu Pro His Pro Tyr His Gly Ala Ile Trp Thr Glu Val Trp Glu
930                 935                 940

<210> SEQ ID NO 8
<211> LENGTH: 874
<212> TYPE: PRT
<213> ORGANISM: Homo sapiens

<400> SEQUENCE: 8

Met Asp Ser Gly Ala Gly Gly Arg Arg Cys Pro Glu Ala Ala Leu Leu
1               5                   10                  15

Ile Leu Gly Pro Pro Arg Met Glu His Leu Arg His Ser Pro Gly Pro
            20                  25                  30

Gly Gly Gln Arg Leu Leu Leu Pro Ser Met Leu Leu Ala Leu Leu Leu
        35                  40                  45

Leu Leu Ala Pro Ser Pro Gly His Ala Thr Arg Val Val Tyr Lys Val
    50                  55                  60

Pro Glu Glu Gln Pro Pro Asn Thr Leu Ile Gly Ser Leu Ala Ala Asp
65                  70                  75                  80

Tyr Gly Phe Pro Asp Val Gly His Leu Tyr Lys Leu Glu Val Gly Ala
                85                  90                  95

Pro Tyr Leu Arg Val Asp Gly Lys Thr Gly Asp Ile Phe Thr Thr Glu
            100                 105                 110

Thr Ser Ile Asp Arg Glu Gly Leu Arg Glu Cys Gln Asn Gln Leu Pro
        115                 120                 125

Gly Asp Pro Cys Ile Leu Glu Phe Glu Val Ser Ile Thr Asp Leu Val
    130                 135                 140

Gln Asn Gly Ser Pro Arg Leu Leu Glu Gly Gln Ile Glu Val Gln Asp
145                 150                 155                 160

Ile Asn Asp Asn Thr Pro Asn Phe Ala Ser Pro Val Ile Thr Leu Ala
                165                 170                 175

Ile Pro Glu Asn Thr Asn Ile Gly Ser Leu Phe Pro Ile Pro Leu Ala
```

-continued

```
            180                 185                 190
Ser Asp Arg Asp Ala Pro Asn Gly Val Ala Ser Tyr Glu Leu Gln
            195                 200                 205
Ala Gly Pro Glu Ala Gln Glu Leu Phe Gly Leu Gln Val Ala Glu Asp
            210                 215                 220
Gln Glu Glu Lys Gln Pro Gln Leu Ile Val Met Gly Asn Leu Asp Arg
225                 230                 235                 240
Glu Arg Trp Asp Ser Tyr Asp Leu Thr Ile Lys Val Gln Asp Gly Gly
                    245                 250                 255
Ser Pro Pro Arg Ala Ser Ser Ala Leu Leu Arg Val Thr Val Leu Asp
                    260                 265                 270
Thr Asn Asp Asn Ala Pro Lys Phe Glu Arg Pro Ser Tyr Glu Ala Glu
                    275                 280                 285
Leu Ser Glu Asn Ser Pro Ile Gly His Ser Val Ile Gln Val Lys Ala
                    290                 295                 300
Asn Asp Ser Asp Gln Gly Ala Asn Ala Glu Ile Glu Tyr Thr Phe His
305                 310                 315                 320
Gln Ala Pro Glu Val Val Arg Arg Leu Leu Arg Leu Asp Arg Asn Thr
                    325                 330                 335
Gly Leu Ile Thr Val Gln Gly Pro Val Asp Arg Glu Asp Leu Ser Thr
                    340                 345                 350
Leu Arg Phe Ser Val Leu Ala Lys Asp Arg Gly Thr Asn Pro Lys Ser
                    355                 360                 365
Ala Arg Ala Gln Val Val Thr Val Lys Asp Met Asn Asp Asn Ala
                    370                 375                 380
Pro Thr Ile Glu Ile Arg Gly Ile Gly Leu Val Thr His Gln Asp Gly
385                 390                 395                 400
Met Ala Asn Ile Ser Glu Asp Val Ala Glu Thr Ala Val Ala Leu
                    405                 410                 415
Val Gln Val Ser Asp Arg Asp Glu Gly Glu Asn Ala Ala Val Thr Cys
                    420                 425                 430
Val Val Ala Gly Asp Val Pro Phe Gln Leu Arg Gln Ala Ser Glu Thr
                    435                 440                 445
Gly Ser Asp Ser Lys Lys Lys Tyr Phe Leu Gln Thr Thr Thr Pro Leu
                    450                 455                 460
Asp Tyr Glu Lys Val Lys Asp Tyr Thr Ile Glu Ile Val Ala Val Asp
465                 470                 475                 480
Ser Gly Asn Pro Pro Leu Ser Ser Thr Asn Ser Leu Lys Val Gln Val
                    485                 490                 495
Val Asp Val Asn Asp Asn Ala Pro Val Phe Thr Gln Ser Val Thr Glu
                    500                 505                 510
Val Ala Phe Pro Glu Asn Asn Lys Pro Gly Glu Val Ile Ala Glu Ile
                    515                 520                 525
Thr Ala Ser Asp Ala Asp Ser Gly Ser Asn Ala Glu Leu Val Tyr Ser
                    530                 535                 540
Leu Glu Pro Glu Pro Ala Ala Lys Gly Leu Phe Thr Ile Ser Pro Glu
545                 550                 555                 560
Thr Gly Glu Ile Gln Val Lys Thr Ser Leu Asp Arg Glu Gln Arg Glu
                    565                 570                 575
Ser Tyr Glu Leu Lys Val Val Ala Ala Asp Arg Gly Ser Pro Ser Leu
                    580                 585                 590
Gln Gly Thr Ala Thr Val Leu Val Asn Val Leu Asp Cys Asn Asp Asn
                    595                 600                 605
```

-continued

```
Asp Pro Lys Phe Met Leu Ser Gly Tyr Asn Phe Ser Val Met Glu Asn
    610                 615                 620
Met Pro Ala Leu Ser Pro Val Gly Met Val Thr Val Ile Asp Gly Asp
625                 630                 635                 640
Lys Gly Glu Asn Ala Gln Val Gln Leu Ser Val Glu Gln Asp Asn Gly
                645                 650                 655
Asp Phe Val Ile Gln Asn Gly Thr Gly Thr Ile Leu Ser Ser Leu Ser
                660                 665                 670
Phe Asp Arg Glu Gln Gln Ser Thr Tyr Thr Phe Gln Leu Lys Ala Val
            675                 680                 685
Asp Gly Gly Val Pro Pro Arg Ser Ala Tyr Val Gly Val Thr Ile Asn
    690                 695                 700
Val Leu Asp Glu Asn Asp Asn Ala Pro Tyr Ile Thr Ala Pro Ser Asn
705                 710                 715                 720
Thr Ser His Lys Leu Leu Thr Pro Gln Thr Arg Leu Gly Glu Thr Val
                725                 730                 735
Ser Gln Val Ala Ala Glu Asp Phe Asp Ser Gly Val Asn Ala Glu Leu
                740                 745                 750
Ile Tyr Ser Ile Ala Gly Gly Asn Pro Tyr Gly Leu Phe Gln Ile Gly
                755                 760                 765
Ser His Ser Gly Ala Ile Thr Leu Glu Lys Glu Ile Glu Arg Arg His
    770                 775                 780
His Gly Leu His Arg Leu Val Val Lys Val Ser Asp Arg Gly Lys Pro
785                 790                 795                 800
Pro Arg Tyr Gly Thr Ala Leu Val His Leu Tyr Val Asn Glu Thr Leu
                805                 810                 815
Ala Asn Arg Thr Leu Leu Glu Thr Leu Leu Gly His Ser Leu Asp Thr
                820                 825                 830
Pro Leu Asp Ile Asp Ile Ala Gly Asp Pro Glu Tyr Glu Arg Ser Lys
            835                 840                 845
Gln Arg Gly Asn Ile Leu Phe Gly Val Val Ala Gly Val Val Ala Val
    850                 855                 860
Ala Leu Leu Ile Ala Leu Ala Val Leu Val
865                 870
```